US00PP32961P2

(12) United States Plant Patent
Verduin

(10) Patent No.: US PP32,961 P2
(45) Date of Patent: Apr. 6, 2021

(54) ***ASTILBE* PLANT NAMED 'RAZZLE DAZZLE'**

(50) Latin Name: ***Astilbe arendsii* X *Astilbe chinensis***
Varietal Denomination: Razzle Dazzle

(71) Applicant: Harrie Verduin, Heemskerk (NL)

(72) Inventor: Harrie Verduin, Heemskerk (NL)

(73) Assignee: COMPASS PLANTS B.V., Hillegom (NL)

( * ) Notice: Subject to any disclaimer, the term of this patent is extended or adjusted under 35 U.S.C. 154(b) by 0 days.

(21) Appl. No.: 16/873,620

(22) Filed: May 21, 2020

(30) Foreign Application Priority Data

Feb. 1, 2020 (QZ) ..... PBR 20200351

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
See application file for complete search history.

*Primary Examiner* — Susan McCormick Ewoldt
(74) *Attorney, Agent, or Firm* — C. A. Whealy

(57) ABSTRACT

A new and distinct cultivar of *Astilbe* plant named 'Razzle Dazzle', characterized by its broadly upright and mounding plant habit; vigorous growth habit; dense and bushy appearance; dark green-colored leaves; freely and uniformly flowering habit; light and dark pink-colored flowers on strong, tall and upright peduncles; and good container and garden performance.

2 Drawing Sheets

Figure 1:
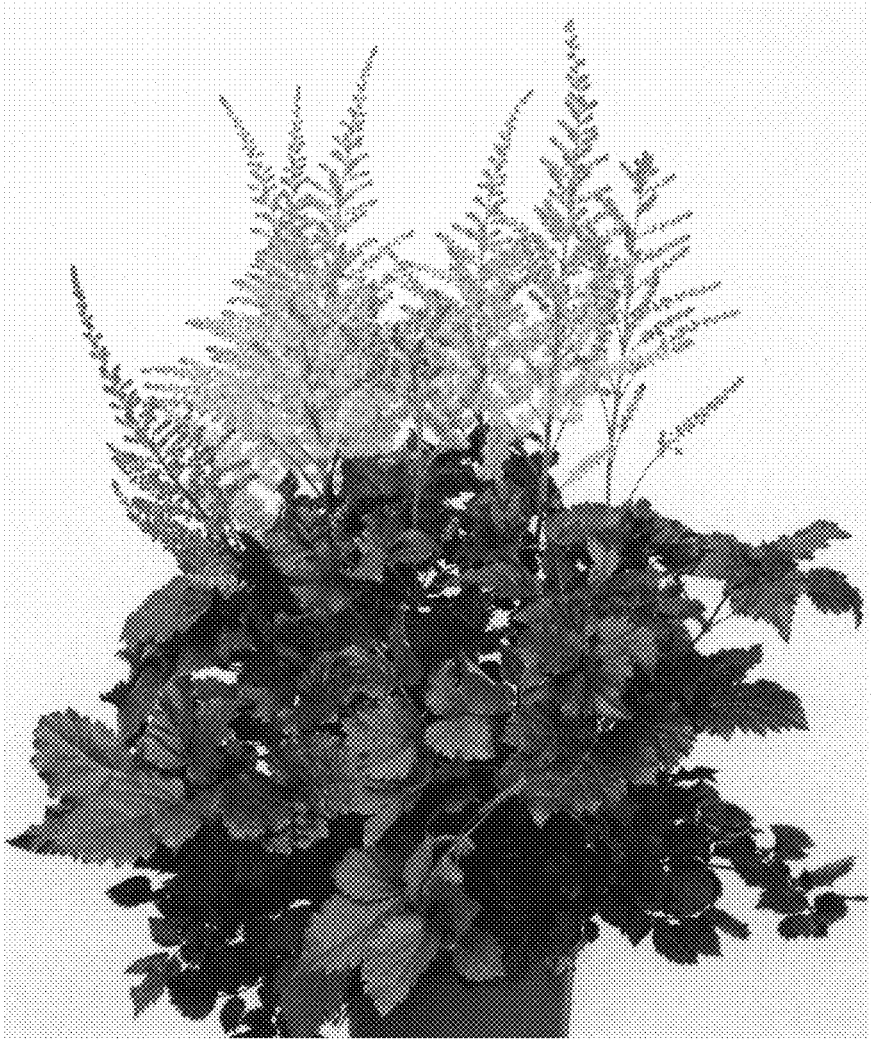

Botanical designation: *Astilbe arendsii* X *Astilbe chinensis*.

Cultivar denomination: 'RAZZLE DAZZLE'.

CROSS-REFERENCE TO A RELATED APPLICATION AND STATEMENT REGARDING PRIOR DISCLOSURES BY INVENTOR/APPLICANT

This application claims priority to a European Community Plant Breeders' Rights application filed on Feb. 1, 2020, application number 20200351. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Astilbe*, botanically known as *Astilbe arendsii* X *Astilbe chinensis* and hereinafter referred to by the name 'Razzle Dazzle'.

The new *Astilbe* plant is a product of a planned breeding program conducted by the Inventor in Heemskerk, The Netherlands. The objective of the breeding program was to create new uniform and freely flowering *Astilbe* plants with attractive leaf and flower coloration.

The new *Astilbe* plant originated from a cross-pollination in 2013 in Heemskerk, The Netherlands, of an unidentified seedling selection of *Astilbe arendsii*, not patented, as the female, or seed, parent with an unidentified seedling selection of *Astilbe chinensis*, not patented, as the male, or pollen, parent. The new *Astilbe* plant was discovered and selected by the Inventor as a single flowering plant from within the progeny of the stated cross-pollination in a controlled greenhouse environment in Heemskerk, The Netherlands during the summer of 2015.

Asexual reproduction of the new *Astilbe* plant by vegetative divisions in a controlled nursery environment in Heemskerk, The Netherlands since December, 2015, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Razzle Dazzle'. These characteristics in combination distinguish 'Razzle Dazzle' as a new and distinct *Astilbe* plant:

1. Broadly upright and mounding plant habit.
2. Vigorous growth habit.
3. Dense and bushy appearance.
4. Dark green-colored leaves.
5. Freely and uniformly flowering habit.

6. Light and dark pink-colored flowers on strong, tall and upright peduncles.
7. Good container and garden performance.

Plants of the new *Astilbe* differ primarily from plants of the selections in plant habit as plants of the new *Astilbe* are more compact than plants of the parent selections. In addition, plants of the new *Astilbe* are more freely flowering than plants of the parent selections.

Plants of the new *Astilbe* can be compared to plants of *Astilbe arendsii* 'Bressingham Ruby', not patented. In side-by-side comparisons, plants of the new *Astilbe* and 'Bressingham Ruby' differ primarily in the following characteristics:

1. Plants of the new *Astilbe* are more compact and bushier than plants of 'Bressingham Ruby'.
2. Inflorescences of plants of the new *Astilbe* are smaller than inflorescences of plants of 'Bressingham Ruby'.
3. Flowers of plants of the new *Astilbe* are light pink and dark pink in color than flowers of plants of 'Bressingham Ruby' which are solid pink in color.

Plants of the new *Astilbe* can be compared to plants of *Astilbe chinensis* 'Vision in Pink', disclosed in U.S. Plant Pat. No. 11,860. In side-by-side comparisons, plants of the new *Astilbe* and 'Vision in Pink' differ primarily in the following characteristics:

1. Plants of the new *Astilbe* are more compact and bushier than plants of 'Vision in Pink'.
2. Inflorescences of plants of the new *Astilbe* are smaller than inflorescences of plants of 'Vision in Pink'.
3. Flowers of plants of the new *Astilbe* are light and dark pink in color whereas flowers of plants of 'Vision in Pink' are solid pink in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1 of 2) is a side perspective view of a typical flowering plant of 'Razzle Dazzle' grown in a container.

Figure 2:
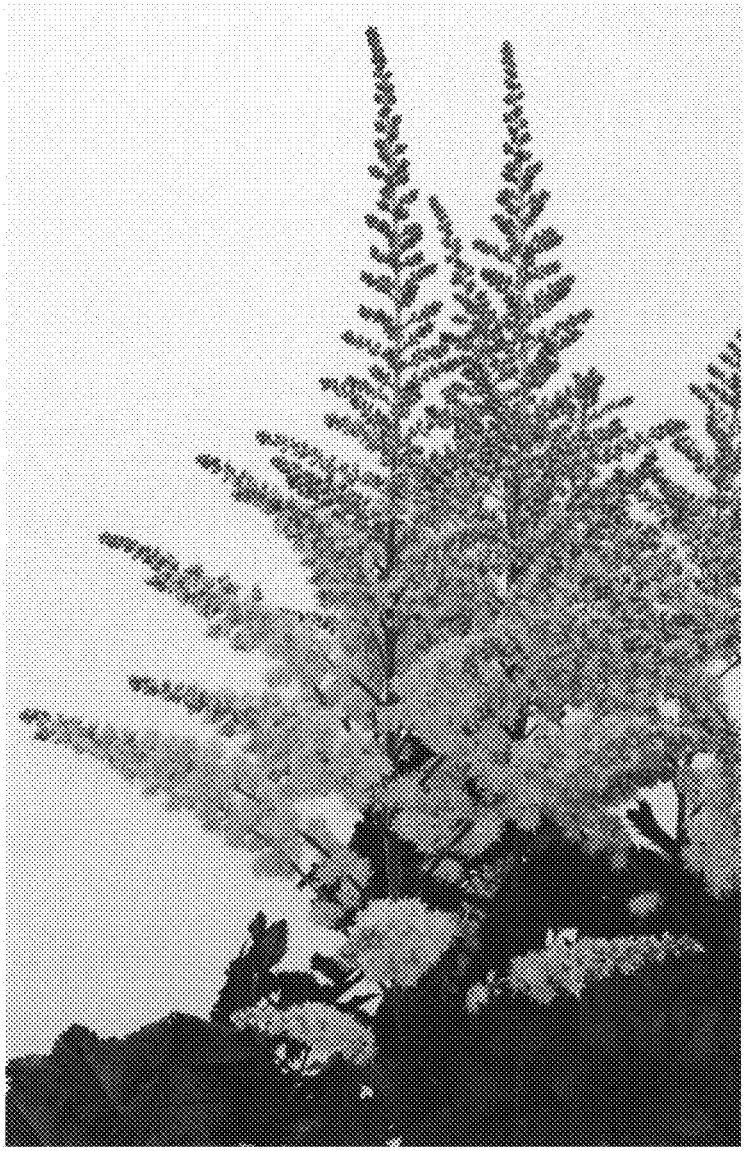

The photograph on the second sheet (FIG. 2 of 2) is a close-up view of typical inflorescences of 'Razzle Dazzle'.

DETAILED BOTANICAL DESCRIPTION

The aforementioned photographs and following observations, measurements and values describe plants grown during the summer in 19-cm containers in an outdoor nursery in Heemskerk, The Netherlands and under cultural practices typical of commercial *Astilbe* production. During the production of the plants, day temperatures ranged from 20° C. to 40° C. and night temperatures ranged from 8° C. to 24° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe arendsii* X *Astilbe chinensis* 'Razzle Dazzle'.

Parentage:

*Female, or seed, parent*.—Unidentified *Astilbe arendsii* seedling selection, not patented.

*Male, or pollen, parent*.—Unidentified *Astilbe chinensis* seedling selection, not patented.

Propagation:

*Type*.—By vegetative divisions.

*Time to initiate roots*.—About three weeks at temperatures about 20° C.

*Root description*.—Thick, fleshy; typically brown in color, actual color of the roots is dependent on substrate composition, water quality, fertilizer type and formulation.

*Rooting habit*.—Freely branching; dense.

Plant description:

*Plant form and growth habit*.—Herbaceous perennial; broadly upright and mounding plant form with inflorescences held above the foliar plane; flowering stems and leaves basal; freely flowering with numerous basal branches developing per plant, dense and bushy; vigorous growth habit; and freely and uniformly flowering habit.

*Growth rate*.—Moderately rapid to rapid; from divisions, about three months are required to produce fully-grown flowering plants in containers.

*Plant height* (*soil level to top of foliar plane*).—About 35 cm.

*Plant height* (*soil level to top of inflorescences*).—About 62.5 cm.

*Plant width* (*spread*).—About 66 cm.

*Stem description*.—Length: About 25.3 cm. Diameter: About 4 mm. Internode length: About 6.8 cm. Strength: Strong. Aspect: Erect to about 20° from vertical. Texture and luster: Sparsely pubescent; slightly glossy. Color, developing: Close to 182B. Color, developed: Close to 146A to 146B.

Leaf description:

*Arrangement*.—Alternate; biternately compound; on average, about 27 leaflets per leaf.

*Leaf length* (*excluding petiole*).—About 21.9 cm.

*Leaf width*.—About 24.7 cm.

*Terminal leaflet length*.—About 7.8 cm.

*Terminal leaflet width*.—About 6.2 cm.

*Lateral leaflet length*.—About 4.6 cm.

*Lateral leaflet width*.—About 3.6 cm.

*Leaf shape, in outline*.—Broadly ovate to broadly deltoid.

*Leaflet shape*.—Broadly ovate.

*Leaflet apex*.—Apiculate to broadly acuminate.

*Leaflet base*.—Short attenuate to short cuneate.

*Leaflet margin*.—Biserrate; moderately undulate.

*Leaflet texture and luster, upper and lower surfaces*.—Moderately pubescent; moderately glossy.

*Leaflet venation pattern*.—Pinnate.

*Leaflet color*.—Developing leaflets, upper surface: Darker than between 143A and 144A. Developing leaflets, lower surface: Close to between 138A and 146A. Fully expanded leaflets, upper surface: Close to between 147A and N189A; venation, close to 144A. Fully expanded leaflets, lower surface: Close to NN137C; venation, close to 145A.

*Leaf petiole length*.—About 26.2 cm.

*Leaf petiole diameter*.—About 3 mm.

*Leaf and leaflet petiole strength*.—Strong.

*Leaf and leaflet petiole texture and luster, upper and lower surfaces*.—Moderately pubescent; slightly glossy.

*Leaf and leaflet petiole color, upper surface*.—Close to 144A; at the nodes, close to 176B.

*Leaf and leaflet petiole color, lower surface*.—Close to 144B.

Flower description:

*Flower type and flowering habit*.—Single rotate flowers arranged on terminal compound panicles; flowers face upright, outward or downward depending on position on the inflorescence; panicles conical in shape; freely and uniformly flowering habit with about 3,000 flowers developing per inflorescence and about 24,000 flowers developing per plant during the flowering season.

*Fragrance*.—Faint to moderate; sweet and somewhat moldy and pleasant.

*Natural flowering season*.—Plants begin flowering about 13 weeks after planting; continuously flowering from late spring until late summer in The Netherlands.

*Postproduction longevity*.—Flowers last about ten days on the plant; flowers not persistent.

*Flower buds*.—Height: About 3 mm. Diameter: About 2.25 mm. Shape: Broadly ovate. Texture and luster: Smooth, glabrous; matte. Color: Sepals, close to 143B and petals, close to N57B to N57C.

*Inflorescence height*.—About 32.2 cm.

*Inflorescence diameter*.—About 21.4 cm.

*Flower diameter*.—About 7 mm.

*Flower depth*.—About 4 mm.

*Petals*.—Quantity per flower: Typically five in a single whorl. Length: About 4 mm. Width: About 0.75 mm. Shape: Oblanceolate. Apex: Obtuse. Base: Narrowly cuneate. Margin: Entire; not undulate. Texture and luster, upper and lower surfaces: Smooth, glabrous; slightly glossy. Color: Developing petals, upper and lower surfaces: Close to 75D; towards the margins, close to 75C. Fully expanded petals, upper and lower surfaces: Close to N155B; color does not change with development.

*Sepals*.—Quantity per flower: Typically five in a single whorl, lower 30% fused towards the base forming a campanulate-shaped calyx. Length: About 2 mm. Width: About 1 mm. Shape: Ovate. Apex: Bluntly acute. Base: Cuneate, fused. Margin: Entire. Texture and luster, upper and lower surfaces: Smooth, glabrous; matte. Color: Developing sepals, upper surface: Close to 143B; apex tinged with close to N57C. Developing sepals, lower surface: Close to 143B; apex, close to N57B. Fully expanded sepals, upper surface: Close to 155D; apex tinged with close to N57D; colors do not change with development. Fully expanded sepals, lower surface: Close to 155D; apex, close to N57D; colors do not change with development.

*Peduncles*.—Length: About 32 cm. Diameter: About 4 mm. Angle: Mostly erect. Strength: Strong. Texture and luster: Densely pubescent; matte. Color: Close to 146B.

*Pedicels*.—Length: About 1 mm. Diameter: About 0.5 mm. Angle: About 45° from peduncle axis. Strength: Moderately strong. Texture and luster: Moderately pubescent; matte. Color: Close to 155C.

*Reproductive organs*.—Stamens: Quantity per flower: Typically ten; anthers basifixed. Filament length: About 2 mm. Filament color: Close to N155A. Anther shape: Broadly ovate. Anther length: About 0.3 mm. Anther diameter: About 0.2 mm. Anther color: Close to NN155A. Pollen amount: Scarce. Pollen color: Close to 155A. Pistils: Quantity per flower: Two or three. Pistil length: About 2 mm. Stigma diameter: About 0.2 mm. Stigma shape: Club-shaped. Stigma color: Close to 70B. Style length: About 1.8 mm. Style color: Close to 68C to 68D. Ovary color: Close to 155A.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25° to 35° C. and to be suitable for USDA Hardiness Zones 5 through 10.

It is claimed:

1. A new and distinct *Astilbe* plant named 'Razzle Dazzle' as illustrated and described.

* * * * *